United States Patent [19]

O'Neill

[11] Patent Number: 5,698,409
[45] Date of Patent: Dec. 16, 1997

[54] MONOCLONAL ANTIBODIES TO THYMIDINE KINASE 1 AND USES IN DIAGNOSTIC AND THERAPEUTIC APPLICATIONS

[75] Inventor: Kim L. O'Neill, Orem, Utah

[73] Assignee: Brigham Young University, Provo, Utah

[21] Appl. No.: 438,627

[22] Filed: May 10, 1995

Related U.S. Application Data

[63] Continuation-in-part of Ser. No. 152,429, Nov. 12, 1993, abandoned, which is a continuation-in-part of Ser. No. 136,299, Oct. 14, 1993, abandoned, which is a continuation of Ser. No. 102,735, Aug. 6, 1993, abandoned.

[51] Int. Cl.$^6$ .................. G01N 33/574; G01N 33/573; G01N 16/40; G01N 16/30
[52] U.S. Cl. .................. 435/7.23; 435/7.4; 435/7.9; 530/388.26; 530/388.8; 530/388.85; 436/64
[58] Field of Search .................. 435/7.4, 7.23, 435/7.9; 436/64, 813; 530/388.26, 388.8, 388.85

[56] References Cited

U.S. PATENT DOCUMENTS 4,317,877 3/1982 Balis et al. .................. 435/7.23

FOREIGN PATENT DOCUMENTS 0 255 431 B1 10/1991 European Pat. Off. .

OTHER PUBLICATIONS

Sherley, J.L. and Kelly, T.J., "Human Cytosolic Thymidine Kinase," J. Biol. Chem. (1988) 263(1):375–382.

Munch–Petersen, B., "Thymidine Kinase in Human Leukemia—Expression of Three isoenzyme Variants in Six Patients with Chronic Myelocytic Leukemia," Leukemia Research (1990) 14(1):39–45.

Munch–Petersen, B. et al., "Diverging Substrate Specificity of Pure Human Thymidine Kinases 1 and 2 Against Antiviral Dideoxynucleosides," J. Biol. Chem. (1991) 266(14):9032–9038.

Ellims, P.H. et al., "Human thymidine kinase: purification and some properties of the TK1 isoenzyme from placenta," Mol. Cell. Biochem. (1982) 45:113–116.

Gan, T.E. et al., "Human Thymidine Kinase—Purification and Properties of the Cytosolic Enzyme of Placenta," J. Biol. Chem. (1983) 258(11):7000–7004.

Tamiya, N. et al., "Co–purification of thymidylate kinase and cytosolic thymidine kinase from human term placenta by affinity chromatography,"Biochimica et Biophysica Acta (1989) 995:28–35.

Bronzert, D.A. et al., "Purification and Properties of Estrogen–responsive cytoplasmic Thymidine Kinase from Human Breast Cancer," Cancer Res. (1981) 41:604–610.

Baron, G. et al., "A Rapid Two–Step Purification of Rat Liver Fetal Thymidine Kinase," Preparative Biochem. (1990) 20(3&4):241–256.

Flemington, E. et al., "Sequence, structure and promoter characterization of the human thymidine kinase gene," Gene (1987) 52:267–277.

O'Neill, K.L. et al., "Elevated serum and mononuclear leukocyte thymidine kinase activities in patients with cancer," Irish Med. J. (1987) 80(9):264–265.

O'Neill, K.L. et al., "Can Thymidine Kinase Levels in Breast Tumors Predict Disease Recurrence?", Reports (1992) 84(23):1825–1828).

Hannigan, B.M. et al., "thymidine Kinases: The Enzymes and their Clinical Usefulness," Cancer Biotherapy (1993) 8(3):189–197.

Gronowitz, J.S. et al., "Application of an in vitro Assay for Serum Thymidine Kinase: Results on Viral Disease and Malignancies in Humans," Int. J. Cancer (1984) 33:5.

McKenna, P.G. et al., "Thymidine kinase activities in mononuclear leukocytes and serum from breast cancer patients," Brit. J. Cancer (1988) 57:619–622.

Primary Examiner—Toni R. Scheiner
Attorney, Agent, or Firm—Greenlee, Winner and Sullivan, P.C.

[57] ABSTRACT

The invention provides a method for the purification of a mammalian thymidine kinase 1. Also provided is a purified mammalian TK1, obtained from Raji cells, that is stable in the absence of stabilizing agents, has a molecular weight of approximately 100 kD and exhibits enzyme activity associated with the native 100 kD tetrameric species of TK1 but not the monomeric subunit. This purified TK1 was used to prepare a monoclonal antibody which inhibited TK1 enzyme activity. This anti-TK1 monoclonal antibody was used in methods for the diagnosis of cancer and for predicting the recurrence of cancer.

26 Claims, 5 Drawing Sheets

MONOCLONAL ANTIBODIES TO THYMIDINE KINASE 1 AND USES IN DIAGNOSTIC AND THERAPEUTIC APPLICATIONS

RELATEDNESS OF THE INVENTION

The subject application is a continuation-in-part of U.S. application Ser. No. 152,429, filed Nov. 12, 1993, now abandoned, which is a continuation-in-part application of application Ser. No. 136,299, filed Oct. 14, 1993, now abandoned, which was a continuation application of application Ser. No. 102,735, filed Aug. 6, 1993, now abandoned.

FIELD OF THE INVENTION

The invention relates generally to a monoclonal antibody to thymidine kinase 1 useful for diagnosis, prognosis and treatment of cancer and certain blood disorders, and to prediction of recurrence in cancer patients.

BACKGROUND OF THE INVENTION

Once a cancer is detected, an important factor in determining the treatment(s) to be used is the stage of development of the disease. Generally, cancers are graded from Stage I, the earliest and most treatable phase, to Stage IV, which is a very advanced, often metastic tumor, with prognosis of death.

Also, it is desirable to monitor the growth or lack thereof of the cancer during and subsequent to a course of treatment. If tumor recurrences are detected very early, they may in some cases be successfully treated to produce an ultimate cure or to significantly prolong the life of the patient. Or, if a tumor is not responding well to a particular drug or treatment, others can be tried.

Taking breast cancer as an example, if it were possible to accurately predict those patients that are liable to exhibit tumor recurrence, then appropriate courses of treatments could be administered dependent on the aggressiveness of the tumor. In cases where the tumor is believed to be very aggressive, then close follow-up is called for with additional surgery, radiotherapy, and possibly chemotherapy. If the tumor is shown not to be aggressive, then a milder course of treatment may be appropriate. Accurate prediction of breast tumor behavior would clearly facilitate better tumor management and contribute significantly to patient well being.

Also, early detection of recurrence would enable the physician to take rapid measures to treat the recurrence and possibly increase the likelihood of patient survival. For breast cancer, it is presently believed that one of the best predictors of the likelihood of recurrence is estrogen receptor status. Those patients who are estrogen receptor positive (high numbers of estrogen receptors on the tumor cells) are thought to have a better prognosis, while those who are estrogen receptor negative are thought to have a poor prognosis. However, there are many cases where those who are estrogen receptor negative do not show recurrence, and those who are estrogen receptor positive do show recurrence. Because the estrogen receptor test is not sufficiently reliable as a prognostic indicator, patients are often treated with both radiotherapy and chemotherapy, regardless of estrogen receptor status.

Thymidine kinase (ATP:thymidine-5' phosphotransferase; EC 2.7.1.21 in the International Union of Biochemistry classification system) is an enzyme that phosphorylates thymidine to thymidine monophosphate (TMP). The commonly used abbreviation of TK will be used herein to denote thymidine kinase in a general sense, where different TK isozymes are not specified particularly.

Thymidine kinase protein has been isolated from many different sources and purified to varying degrees. A variety of different molecular weight thymidine kinases have been reported from human samples, depending on the particular cell and the method of isolation and analysis. In general, the findings suggest that thymidine kinase exists in at least one monomeric form and a variety of multimeric forms.

In humans, it is also known that there are at least two major isozymes (similar but distinct forms) of thymidine kinase, o referred to herein as TK1 and TK2. These isozymes are produced from different genes, are found in different cellular compartments, and differ in their levels and timing of expression during the cell cycle and according to the cell differentiation state. In humans, the TK1 gene is on chromosome 17 in band q21-22 (Elsevier 1974) while the TK2 gene is on chromosome 16 (Willecke et al. (1977) Somatic Cell Genet. 3:237). A gene for TK1 has recently been cloned and sequenced (Lin (1984) Proc. Nat'l Acad. Sci. 81:414–418; Flemington (1987) Gene 52:267–277).

There are reports that TK activity is elevated in the serum or tumor tissues of patients with some kinds of cancer, including but not limited to acute and chronic leukemias, Hodgkins' and non-Hodgkins' lymphomas, and solid tumors of breast, prostate, brain, and rectum [O'Neill et al. (1987) Ir. Med. J. 80:264–265; O'Neill et al., (1992) J. Natl. Cancer Inst. 84:1825–1828; McKenna et al. (1988) Br. J. Cancer 57:619–622; Ellims et al. (1981) Cancer Res. 41:691–695; Ellims et al. (1981) Blood 58:926–930; Kallander et al. (1984) Cancer 54:2450–2455; Eriksson et al. (1985) Acta Rad Oncol. 24:167–171; O'Neill et al. (1986) Ir. J. Med. Science 155:272–274; O'Neill et al. (1986) Tumor Biol. 7:236]. Persistent elevation of thymidine kinase in the serum has been proposed as an indictor of malignant disease. However, the measurement of thymidine kinase activity by conventional means is tedious and not always reproducible.

Furthermore, it is not always clear from previous reports which of the isozymes or forms of thymidine kinase is elevated in activity in cancer patients. The method generally used for measuring the level of TK1 is based on enzyme activity by comparison of incorporation of radioactive thymidine in parallel samples assayed with different secondary substrates (adenosine triphosphate or ATP, and cytosine triphosphate or CTP). Both TK1 and TK2 utilize ATP as the substrate very efficiently. However, the TK1 isozyme has only about 7–15% activity with CTP as substrate as it does with ATP. TK2, however, is nearly as efficient with CTP as with ATP. The levels of total TK activity are determined from the assay with ATP, while the levels of TK2 activity are determined from the assay with CTP. The difference between the activity level measured with CTP and that measured with ATP is attributed to the TK1 isozyme.

This method is tedious, and the results are highly dependent on the precise performance of the parallel assays and sometimes difficult to reproduce. Further, since TK1 does show some incorporation with the CTP substrate, the interpretation can be ambiguous. Also, the active form of the TK1 protein appears to be rather unstable, so the amount of activity detected may vary depending on handling of the sample.

It would thus be desirable to be able to measure the amounts of TK protein and/or of individual TK isozymes. For such purposes, an antibody specific for a TK isozyme, especially a monoclonal antibody to TK1, would be useful. Particularly useful would be a monoclonal antibody to active TK1 capable of neutralizing or inhibiting TK1 enzyme activity. For this purpose a purified and biologically active mammalian TK1 would be required.

There are extensive inconsistent reports in the prior art on the properties of mammalian TK1, with diverging results and observations as to the electrophoretic behavior and kinetic properties. Native molecular weights between 45,000 and 200,000 daltons have been reported for the native human TK1 from, for example, leukemic cells (96 kD, Sherley et al. (1988) J. Biol. Chem 263:375–391; 150–200 kD, Munch-Petersen et al., (1990) Leuk. Res. 14:39–45), human placenta (45 kD, Ellims et al. (1982) Mol. Cell. Biochem. 45:113–116); 92 kD, Gan et al. (1983) J. Biol. Chem. 258:7000–7004; 70 kD, Tamiya et al. (1989) Biochim. Biophys. Acta 995:28–35), lymphocytes (110 kD, Munch-Petersen et al. (1991) J. Biol. Chem. 266:9032–9038), and human breast cancer (177 kD, Bronzert et al. (1981) Cancer Res. 41:604–610).

It has been reported that in the presence of ATP, native TK1 shifts to a form of TK1 having a higher molecular weight, for example, human placental TK1 of 50 kD shifts to 70 kD in the presence of ATP (Tamiya et al. (1989), supra) and human lymphocytic TK1 of 55 kD shifts in the presence of ATP to a form having a molecular weight of 110 kD (Munch-Petersen et al. (1991) supra).

Not only are widely divergent values reported for the molecular weight of the native TK1, different views exist in the prior art for the monomeric subunit of TK1. Molecular weights of 44 and 22–24 kD have been reported for the TK1 monomer. Further, reports vary as to whether the monomeric subunit is associated with TK1 enzymatic activity. For example, TK1 enzyme activity has been reported to be associated with the monomeric subunit of approximately 24 kD for the HeLa cells (Sherley et al. (1988) supra), rat liver (Baron et al. (1990) Preparative Biochemistry 20:241–256), and human lymphocytes (Munch-Petersen (1991) supra), but enzyme activity was not found associated with the monomeric subunit in the presence or absence of ATP for human placenta TK1 (Tamiya et al. (1989) supra).

Almost every report relating to a mammalian purified TK1 describes the high lability of the enzyme as it reached homogeneity. For example, Ellims et al. (1982) supra reported that "At all stages of purification, the enzyme showed irreversible lability" and "Addition of sulfhydryl agents, ATP-MgCl$_2$ or glycerol did not stabilize the enzyme activity." It was also reported that "the catalytic lability of the final enzyme preparation has precluded extensive characterization of its kinetic characteristics and attempts to stabilize this activity were unsuccessful" (Gan et al., 1983, supra).

In almost all prior art references describing purification of TK1, the TK1 was purified using thymidine-affinity chromatography as the critical step in the purification process. The extreme lability for the purified TK1 appeared after the step of thymidine-affinity chromatography, e.g., "The final enzyme preparation was markedly labile, with up to 50% of activity lost with storage at 4° C., 0° C. or –20° C. for 4 hr." (Ellims et al., 1982, supra) and "The enzyme preparation obtained after Step 4 (affinity chromatography) was labile with loss of more than 70% activity in 24 h . . . " (Gan et al., 1983, supra).

Stabilization of TK1 by the addition of digitonin during the purification process was reported by Sherley et al. (1988) J. Biol. Chem. 263:375–382. The total dependence on digitonin for the purified digitonin-stabilized TK1 is described, e.g., "Omission of digitonin in the final column elution buffer resulted in a preparation which lost greater than 50% of its activity after only 2 weeks of storage at –80° C." and "When the purified (digitonin-stabilized) enzyme was electrophoresed in this gel system, the recovery of activity was poor." Similarly, it was reported (Baron et al. (1990) Preparative Biochemistry) that TK1 "eluted in the absence of digitonin was unstable as more than 95% of its activity were lost when the enzyme was lyophilized or thawed after storage at –80° C." Instead of digitonin, Munch-Petersen et al. (1991, J. Biol. Chem. 266:9032–9038) utilized CHAPS (3-[3-cholamido-propyl) dimethylamminio]-1-propane sulfonic acid) as a stabilizing agent during the purification of TK1 from human lymphocytes, stating that "The presence of CHAPS during the last purification steps and storage at –70° C. stabilized both enzymes, whereas more than 80% of the activity was lost in a week at –70° C. in the absence of detergent."

High lability of the purified TK1 precluded sufficient yields of purified enzyme for extensive biochemical characterization studies and for preparation of monoclonal antibodies to an enzymatically-active purified mammalian TK1. There are no published references in the prior art reporting the successful preparation and/or use of monoclonal antibodies to TK1. There are a few reports, however, of immune sera to purified forms of TK1. For example, Gan et al., 1983, supra, reported the preparation of rabbit immune serum to purified human placental TK1 and its cross-reactivity with crude and partially purified placental TK1 but not with human liver crude extract, human liver purified TK1 or placental mitochondrial extract. Thus, the antiserum elaborated with human placental TK1 did not cross react with purified placental or liver TK2. Similarly, rabbit immune serum was prepared with digitonin-stabilized TK1 purified from HeLa cells (Sherley et al., 1998, supra). This serum was non-neutralizing but could be used to precipitate the enzyme in both purified and crude states. The immune serum specifically precipitated a Mr=24,000 polypeptide in extracts of [$^{35}$S] methionine-labeled HeLa cells.

In addition, Balis et al. (U.S. Pat. No. 4,317,877, Mar. 2, 1982) disclosed immunesera to a small subunit component of (a) TK from normal colonic mucosa and (b) TK from term human placenta. Although both small subunit components were electrophoretically similar, they were not antigenically identical as indicated by differences in precipitin patterns. Moreover, it was stated that "The lack of complete neutralization by these antisera of their respective homologous enzymes is not unexpected since only the small molecular weight component is used as antigen." The teaching in the Balis et al. patent, supra, is that an antiserum to a subunit component of TK1 does not completely react with nor neutralize the active multimeric form of the TK1. Also, the Balis antibody did not react with leukemic leukocytes or with normal or mitogen-stimulated peripheral lymphocytes, even though these are known to have elevated TK levels (Balis et al., col. 2, lines 21–23).

Another European Patent publication, No. 0 255 431 by Jouan published Oct. 23, 1991, discloses purification of "TK-F" (fetal TK or TK1) from human placental material for purposes including the use of the pure TK-F to produce anti-TK-F antibodies. Jouan teaches the purification of TK-F using prior art technology which has been shown in various reports to result in the purification of a TK1 so labile that yields of purified TK are insufficient for further manipulation, e.g., for biochemical characterization, monoclonal antibody preparation, screening, etc. Jouan suggests the use of art-known methods to prepare monoclonal antibody using his purified TK-F, however, the patent does not teach how to overcome the problem of extreme lability associated with a purified TK1 obtained using prior art methodologies, a problem noted in many prior art references.

To date there is no documentation for the existence an antibody (neither polyclonal nor monoclonal) to a purified and enzymatically active mammalian TK1 of 100 kD molecular weight that is not combined with a stabilizing agent, and that exhibits enzyme activity associated with the tetrameric 100 kD form and not with the monomeric subunit. The prior art does not disclose an anti-TK1 antibody that completely inhibits TK1 enzyme activity.

Accordingly, a need remains for antibodies useful to detect specifically TK1 as well as the total amounts of thymidine kinase isozymes in serum and tissues. There further remains a need for improved methods to diagnose cancer, to assess treatment efficiency and likelihood of tumor recurrence in breast cancer patients and in patients with other types of tumors.

SUMMARY OF THE INVENTION

It is an object of the invention to provide a purified mammalian thymidine kinase 1 (TK1). This TK1 has a molecular weight of approximately 100 kD, is stable in the absence of a stabilizing agent, and exhibits enzyme activity associated with the native tetrameric species but not the monomeric subunit. Previous reports have disclosed a labile, purified mammalian TK1 in which there is an association of TK1 activity with its monomeric subunit having a molecular weight of approximately 24 kD or approximately 45 kD (Sherley et al. (1988) J. Biol. Chem. 263:375–382, and Ellims et al. (1982) Mol. Cell. Biochem. 45:113–116, respectively).

A specific embodiment of the invention provides a purified TK1 prepared from Raji cells, a cell line that was found to comprise almost exclusively TK1 activity and very little, if any, TK2 activity. The disclosure of a source of human thymidine kinase (TK) that comprises almost exclusively only one TK isozyme (namely, TK1) presents a clear advantage for isolating and purifying the TK1 isozyme.

The present invention provides a method for the purification of TK1 that does not utilize thymidine affinity chromatography and that does not require the addition of a stabilizing agent during purification nor during assay of the TK1. Prior art preparations of TK1 exhibit extreme lability (Gan et al. 9183) J. Biol. Chem 258:7000–7004), particularly after the step of purification using thymidine-labeled, affinity chromatography, resulting in vanishing yields of TK1. The presence of a stabilizing agent (e.g., a detergent such as digitonin (Sherley et al. (1988) J. Biol. Chem. 263:375–382) must be used during the purification procedure to stabilize TK1; the digitonin-stabilized TK1 exhibits enzyme activity associated with the monomeric species. In contrast, the present invention provides a purified TK1 of approximately 100 kD molecular weight that exhibits enzymatic activity associated with the multimeric 100 kD species, but not the monomeric subunit and that is purified in the absence of a stabilizing agent.

It is another object of the invention to provide an antibody, and preferably a monoclonal antibody, to the TK1 of the invention. The anti-TK1 antibody not only binds to TK1 but also inhibits TK1 activity. The prior art does not demonstrate an anti-TK1 antibody to an active purified TK1 of approximately 100 kD molecular weight that inhibits TK1 activity. The prior art (Jouan, European Patent publication No. 0 255 431, Oct. 23, 1991) does not present data documenting the actual preparation of an anti-TK1 antibody, and does not solve the problem of obtaining a purified TK1 that is not extremely labile as reported in the art.

The invention provides specific anti-TK1 antibody monoclonal producing hybridomas. Some of these hybridomas are available as ATCC HB 11432, BH 11433 and HB 11434.

It is a further object of the invention to provide a method for the diagnosis of cancer in a patient exhibiting an elevated level of TK1. This method utilizes the anti-TK1 monoclonal antibody of the invention to determine efficaciously the level of TK1 in a patient sample, e.g., serum, tumor, etc., and to associate an elevated TK1 level in the sample with a diagnosis of cancer. The invention provides improved methods and compositions for diagnosing and staging solid and leukemic and lymphoid tumors and for monitoring treatment efficacy and detecting recurrence of such tumors.

This invention also contemplates the provision of a kit useful for the detection and determination of TK1 in a biological sample. The kit comprises an anti-TK1 monoclonal antibody capable of determining the level of TK1 in the sample. This kit can be used for the diagnosis of cancer in a sample which, upon interaction with the anti-TK1 monoclonal antibody, exhibits an elevated level of TK1.

It is an additional object of the invention to provide a method of predicting the likelihood of recurrence of a tumor in a patient having a primary tumor. The likelihood of recurrence of a tumor in a patient at initial diagnosis is carried out with a method comprising the steps of establishing a normal range for tissue TK1 activity, obtaining a sample of a primary tumor or a body fluid (e.g., serum) from a patient, determining the amount of TK1 enzyme in the patient sample to produce a patient TK1 value, and comparing the patient TK1 value to the normal value; and if it exceeds the normal range by a significant amount, predicting that the tumor is likely to recur, and if it does not significantly exceed the normal range, predicting that recurrence is unlikely. This method utilizes the anti-TK1 monoclonal antibody of the invention to determine the level of TK1 in the primary tumor and to evaluate the extent that the level of TK1 is elevated above the normal value of the TK1 level in a corresponding control sample of the tissue (normal). A TK1 level in the tumor sample that is about two-fold, and preferably between about three- and about fifteen-fold, higher than a normal TK1 level is predictive of a recurrence of the tumor.

This invention also contemplates the provision of a kit useful in predicting the likelihood of recurrence of a tumor in a patient having a primary tumor. The kit comprises an anti-TK1 monoclonal antibody of the invention capable of determining the level of TK1 in a sample of the patient's tumor or body fluid (e.g., serum) and in evaluating the extent to which the level of TK1 in the patient's sample is elevated above a normal TK1 value for corresponding sample of normal tissue or fluid. A TK1 level in the patient sample of about two-fold, and preferably between about three-fold and about fifteen-fold, higher than a normal TK1 value is predictive of a recurrence of the tumor.

This invention provides an additional method of predicting the likelihood of recurrence of a tumor in a patient having a primary tumor. This alternate method utilizes the anti-TK1 monoclonal antibody of the invention as well as anti-TK2 monoclonal antibody to determine the levels of TK1 and TK2 in the primary tumor or in a body fluid of the patient having the primary tumor. A recurrence of the tumor is predicted if the percentage of TK1 is equal to or greater than 40% of the total TK (TK1 and TK2); a nonrecurrence of the tumor is predicted if the percentage of TK1 is less than 40% of the total. A kit comprising anti-TK1 as well as anti-TK2 antibodies is also contemplated by this invention for use in predicting the likelihood of recurrence of a tumor in a patient having a primary tumor.

DETAILED DESCRIPTION OF THE PREFERRED EMBODIMENTS

Figure 1:
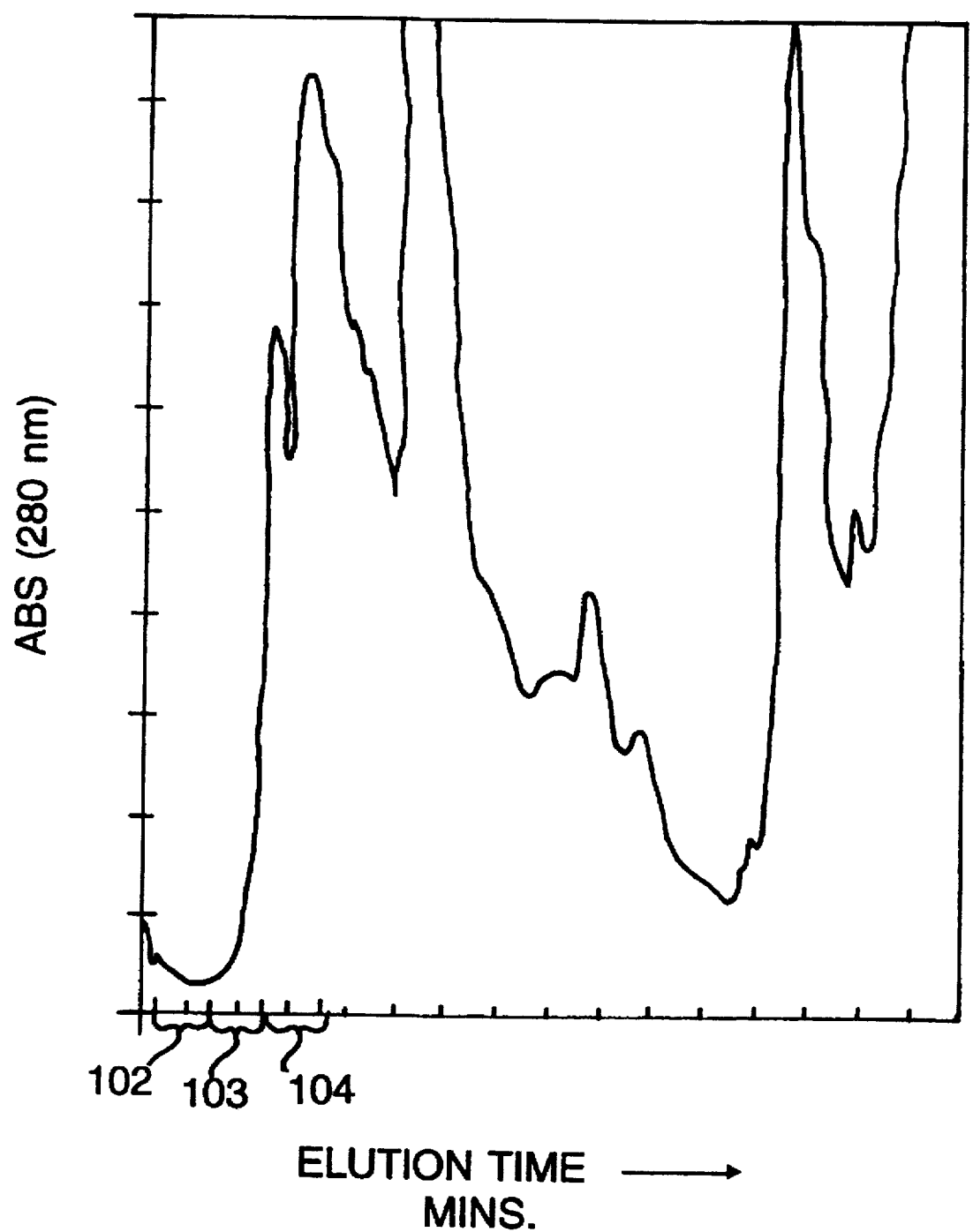
FIG. 1 is a chart depicting absorbance at 280 nm plotted versus elution time from a DEAE-cellulose column of a crude extract of TK1 prepared from Raji cells according to the invention.

The following definitions are provided in order to provide clarity as to the intent or scope of their usage in the specification and claims.

The term purified mammalian thymidine kinase 1 or TK1 as used herein refers to an enzymatically active TK1 isolated from a mammal, including, but not limited to, a mammalian body organ, tissue, cell, fluid and the like, in either normal or diseased condition, and presented as a fresh or preserved specimen, a cell tissue culture, a cell line, a hybridoma, etc. The purified TK1 of the invention is stable in the absence of a stabilizing agent, enabling a yield of purified TK1 sufficient for the preparation of monoclonal antibodies to purified TK1. The purified TK1 is enzymatically active as a native tetrameric species of approximately 100 kD molecular weight and not as a monomeric subunit.

The term mammalian as used herein refers to a human or other animal classified as a mammal.

The term mammalian body sample as used herein refers to a sample from a mammal, including, but not limited to, a body organ, tissue, cell, fluid, etc., in either normal or diseased condition and presented as a fresh or preserved specimen.

The term body fluid as used herein refers to any fluid obtained from a mammal, for example, blood, serum, urine, spinal fluid, tears, etc.

The term body tissue as used herein refers to any normal or diseased tissue obtained from a mammal, for example, organ tissue, biopsy tissue, tumors, etc. A body tissue may be presented as a fresh or preserved (e.g., frozen) sample, a histological slide preparation, etc.

The term stable in the absence of a stabilizing agent as used herein refers to a purified TK1 that is not associated with a stabilizing agent and that was not purified in the presence of a stabilizing agent. The addition of a stabilizing agent is not required in order to demonstrate enzymatic activity for the purified TK1 of the invention. The purified TK1 is deemed to be stable, as judged by measurement of its enzyme activity or its ability to produce a monoclonal antibody capable of inhibiting TK1 activity.

The term stabilizing agent as used herein refers to a compound that must be added in order to demonstrate enzymatic activity for a purified TK1 preparation. (See, Munch-Petersen et al. (1991) J. Biol. Chem. 266:9032–9038 and Sherley et al. (1988) J. Biol. Chem. 263:375–382.) Stabilizing agents contemplated by this invention include, but are not limited to, digitonin, CHAPS, cholic acid derivatives, membrane solubilizing compounds, etc.

The term exhibiting enzymatic activity as a native tetrameric species but not as a monomeric subunit as used herein refers to the association of TK1 activity with the 100 kD TK1 species but not with the monomeric subunit. The monomeric subunit, even in the presence of ATP, does not reconstitute fully into the active 100 kD TK1 species of the invention, as judged by the inability to demonstrate equivalent TK1 activity for the monomeric subunit as for the 100 kD TK1 species, i.e., where the monomeric subunit lacks enzyme activity essentially comparable or equivalent to that associated with the 100 kD tetrameric species on a weight or molar basis.

The term not purified using thymidine affinity chromatography as used herein refers to a purification scheme used to purify TK1 in which the step comprising affinity chromatography on a thymidine linked support (e.g., as described in Bronzert et al. (1981) Cancer Res. 41:604–610; Sherley et al. (1988) J. Biol. Chem. 263:375–382) is not utilized.

The term monoclonal antibody to TK1 or TK1 monoclonal antibody or anti-AcTK1 antibody or anti-TK1 antibody as used herein refers to a monoclonal antibody that binds to an active, 100 kD TK1 and inhibits the TK1 activity. The monoclonal antibody to TK1 exists in various forms, e.g., IgG, IgM, etc. It is contemplated that in some applications a polyclonal antibody to a purified TK1 of the instant invention can be utilized in place of an anti-TK1 monoclonal antibody of the invention.

The term anti-AcTK1 antibody as used herein refers to a monoclonal antibody that binds specifically to an active, 100 kD TK1 and inhibits TK1 activity.

In the development of an antibody specific for TK1 several difficulties were encountered. The TK1 enzyme is labile, so it is difficult to prepare it in sufficient purity and amount for use as an antigen. Because of its lability, the active multimer form of TK1 is changed or degraded to inactive forms of TK1 which, if injected into a mouse, direct B-cells to make antibodies specific to the inactive forms of TK1. Thus, the probability of obtaining a hybridoma producing antibodies capable of inhibiting the active native TK1 is severely reduced. Further, mice have a TK1 enzyme, so it is difficult to elicit an antibody-forming response to TK1 protein.

In order to obtain an anti-TK1 monoclonal antibody capable of inhibiting TK1, an active multimeric form of TK1 must be available and a method for the purification of such an active multimeric TK1 is required. The present invention as described herein enables the preparation of an anti-TK1 monoclonal antibody (a) because it makes available an antigen that is a stable multimeric form of TK1 that is biologically active and (b) because it provides a method of purifying an active multimeric form of TK1 that overcomes the problems associated with the purification methods of the prior art.

It is shown herein that when a tetrameric form of TK1 loses its enzyme activity, its antigenicity (but not its tetrameric character) changes. For this reason, among others, it is necessary to use a purified active multimeric form of TK1 for the elaboration of an anti-TK1 antibody that will be capable of inhibiting TK1.

As part of the invention, it was discovered that Raji cells appear to produce only a single TK isozyme, the TK1. Raji cells are an immortalized human lymphoma cell line, available from ATCC as cell line #CCL-86. The discovery of this pure antigen preparation was helpful in overcoming some of the obstacles which have interfered with previous attempts to produce anti-TK1 antibodies.

It will be appreciated by those of ordinary skill in the art that the objects of this invention can be achieved without the expense of undue experimentation using well known variants, modifications, or equivalents of the methods and techniques described herein. The skilled artisan will also appreciate that alternative means, other than those specifically described, are available in the art to achieve the functional features of the molecules described herein and how to employ those alternatives to achieve functional equivalents of the molecules of the present invention. It is intended that the present invention include those variants, modifications, alternatives, and equivalents which are appreciated by the skilled artisan and encompassed by the spirit and scope of the present disclosure.

The following examples are provided to better elucidate the practice of the present invention and should not be interpreted in any way to limit the scope of the present invention. Those skilled in the art will recognize that various modifications can be made to the methods and formulations described herein while not departing from the spirit and scope of the present invention.

EXAMPLE 1

Assay of Raji cells for TK1 and TK2 activity

A crude cell extract was prepared from Raji cells as follows. Approximately $10^{11}$ to $10^{12}$ exponentially-growing Raji cells were harvested by centrifugation from the growth medium. The pelleted cells were separated from the supernatant and resuspended in 1–2 mls of extraction buffer containing 0.02M Tris-HCl, pH 7.8, 0.05M $MgCl_2$, and 0.2 mM KCl. The cell suspension was subjected to three freeze-thaw cycles in liquid nitrogen and a 37° C. water bath. The ruptured cell suspension was then centrifuged at 30,000×g for 30 minutes to pellet cellular debris. The supernatant, containing about 50 mg/ml of protein, including TK and other soluble enzymes, was decanted from the pellet and stored frozen at −20° C.

To perform TK assays, 0.2 ml of the crude extract was mixed with an equal amount (0.2 ml) of an assay mixture containing 0.02M Tris-HCl (pH 7.8), $2 \times 10^{-6}$M [$^3$H]-thymidine (85 curies per mmole), 0.002M $MgCl_2$, 0.2M KCl, 0.1M $NH_4Cl$, 0.005M mercaptoethanol, and 0.004M ATP (adenosine triphosphate).

The assay reactions were incubated at 37° C. in a water bath. After 30 minute and 60 minute incubation periods, 0.025 ml samples were removed and spotted onto Whatman DE-81 discs and allowed to dry. The filter discs were washed three times with 0.01M formate for 5 minutes each time, rinsed with distilled water for 5 minutes, followed by rinsing with methanol, and then transferred to scintillation vials containing 4 mls of scintillation counting fluid for measurement of $^3$H radioactivity. A duplicate assay was performed in the same manner but substituting CTP (cytosine triphosphate) for ATP.

The results indicated that the crude extract of Raji cells incorporated 7000–8000 cpm of CTP in 60 minutes, as compared to about 259,000 cpm incorporated with ATP was used as the precursor. These results were considered to indicate that there was no detectable level of TK2 activity in Raji cells. The specific activity of the Raji extract was about 559 cpm/mg protein/min.

EXAMPLE 2

Partial purification of TK1

TK1 enzyme was partially purified from the crude extract of Raji cells of Example 1 by DEAE-cellulose anion exchange chromatography. To obtain the largest yields of TK protein, it is desirable that the cells be in the exponential growth phase when harvested. The protein content of the crude extract was determined using the well-known Bradford assay. A total of about 1.0–2.0 grams of protein from the crude extract was added to a DEAE-cellulose column and washed with 10 void volumes of 0.1M Tris-HCl (pH 8.0) using gravimetric flow. The column was eluted with 0.5M Tris-HCl (pH 8.0), and 1.0 ml fractions were collected.

FIG. 1 depicts the absorbance measured at 280 nm as a function of elution time exemplifying fractions 102, 103, 104. Aliquots of the collected fractions were assayed for TK1 activity generally as described in Example 1. Fraction 104, which approximately spans a first peak 110 in the chromatograph, was found to contain most of the TK1 activity eluted from the column. By pooling and concentrating fraction 104 from about a hundred runs performed as in Example 2, approximately 40 mls of eluant containing about 1.6 mg/ml of TK1 protein were recovered. The approximate specific activity of the pooled DEAE-cellulose preparation was 17,430 cpm per mg protein per minute.

The pooled DEAE-cellulose fractions were concentrated using an Amicon protein concentrator, and a sample was electrophoresed under non-denaturing conditions on a 10% polyacrylamide separation gel with a 4.0% polyacrylamide stacking gel. Approximately 7 bands were visible in the gel, ranging from about 24,000 to about 180,000 daltons in molecular weight (MW). These bands were cut out, the protein eluted from the gel and assayed for TK1 activity in a manner similar to that described in Example 1. Only one band of about 100,000 daltons contained significant TK1 activity. There was no significant TK1 activity in any of the other bands. The 100,000 MW band comprised active TK1, and was used as the antigen to produce anti-TK1 monoclonal antibodies. About 50 µg (micrograms) of this TK1 was recovered from the pooled DEAE-cellulose preparation.

EXAMPLE 3

Purification of TK1 by ROTIFER

Alternatively, TK1 was partially purified by isoelectric focussing of the crude extract using a ROTIFER apparatus purchased from Bio-Rad. The procedure used was that outlined in the ROTIFER manual from Bio-Rad (1990). Six to seven protein bands were observed in the isoelectric gels, one of which had a molecular weight of about 100,000 daltons and exhibited some TK1 activity when assayed as described in the preceding paragraphs. The recovery of activity was rather poor, compared to the methods of Examples 2 and 4.

EXAMPLE 4

Purification by FPLC

A third and presently preferred method of purification of TK1 employs FPLC (Fine Protein Liquid Chromatography) with three sequential purifications on a MONO-Q 5/5 anion exchange column, using different elution gradients for each run. The MONO-Q 5/5 is an ion-exchange column packing commercially available from Pharmacia, having substantially monodispersed bead size and strong anion exchange properties via bound quaternary amine groups which remain charged over the range from pH 2 to pH 12. The column was loaded with 0.1 ml of concentrated DEAE-cellulose fraction from the procedure of Example 2 containing about 1 mg protein, and voided with 10 volumes of Buffer A (50 mM Tris-HCl pH 8.0). The void volume of this column was 1.0 ml. A programmed gradient was set up to gradually increase the concentration of Buffer B (1.0M NaCl, 50 mM Tris-HCl, pH 8.0) from 0–100% over 20 minutes running at a constant flow rate of 1.0 ml/min.

Figure 2:
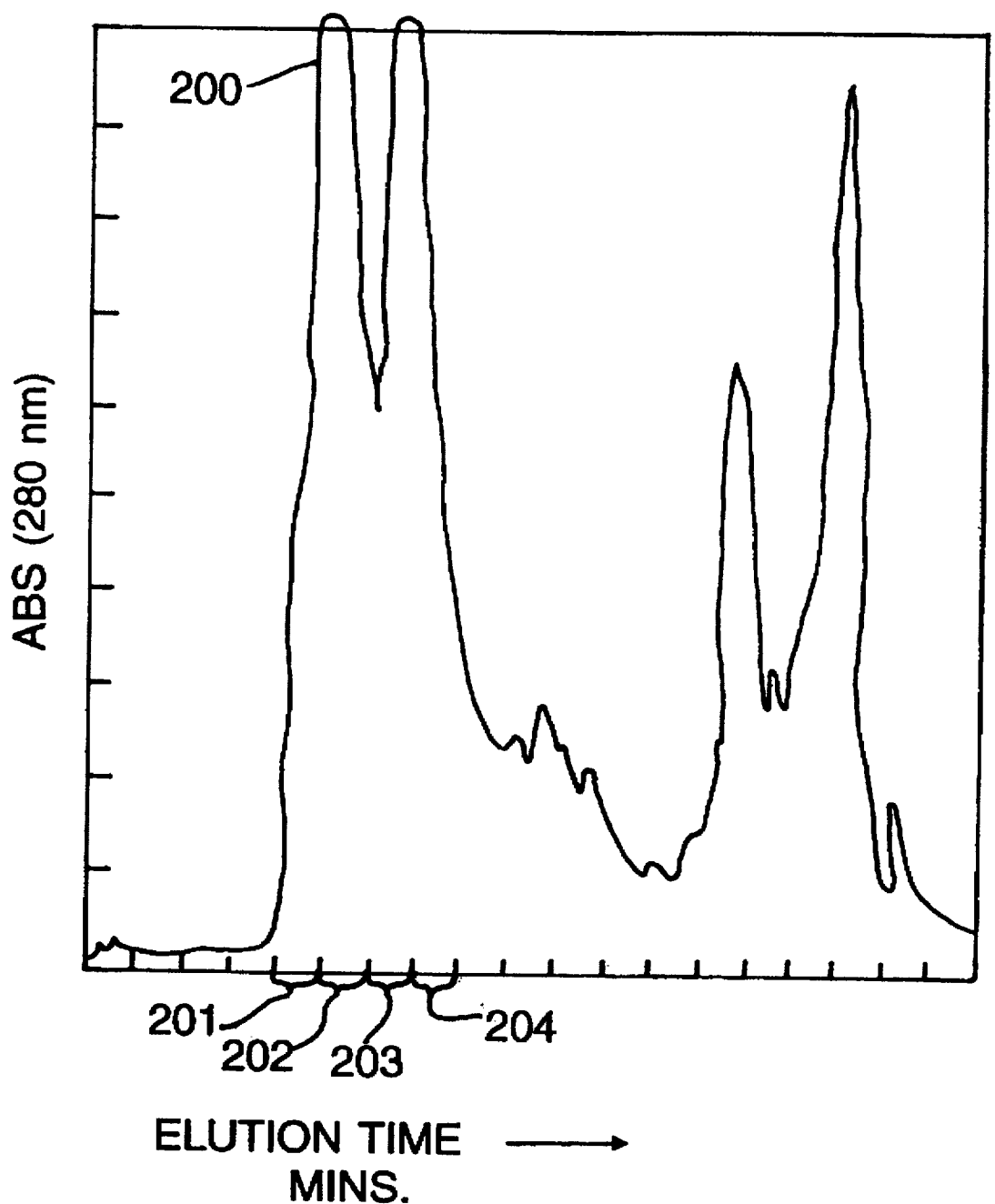
FIG. 2 is a chart depicting absorbance at 280 nm plotted versus elution time from a MONO-Q column of a crude TK1 preparation run as described in Example IV.

The protein was detected as it eluted from the column by absorbance at 280 nm (FIG. 2). Fractions containing the 280 nm absorbance peaks were collected and assayed for TK1 activity as described previously herein. TK1 activity was determined to be primarily in peak 200, which is the first peak eluting from the column, at which point the gradient contained about 15–20% of Buffer B.

Protein from the peak 200 was analyzed by non-denaturing PAGE (polyacrylamide gel electrophoresis) as before to determine purity. There were 5 protein bands present. These bands were cut out and protein from each was assayed for TK1 activity. Detectable TK1 activity was found in the high molecular weight band (100,000 MW), but not in the other bands.

For a second purification step, the fractions having TK1 activity from several runs were collected, pooled and concentrated. This partially purified, pooled sample was then re-run on the MONO-Q column with a lower gradient. One-tenth ml portion of pooled sample containing about 1 mg protein was loaded on the MONO-Q column as before. For this second run, the gradient was started at 5% of Buffer B and ran to 40% Buffer B over 35 minutes at 1.0 ml/min.

Figure 3:
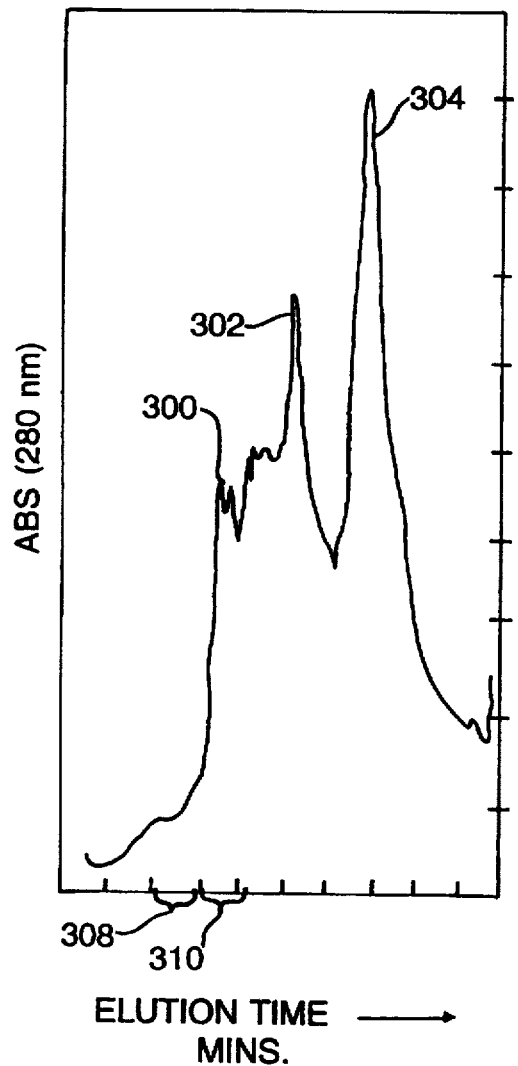
FIG. 3 is a chart depicting absorbance at 280 nm plotted versus elution time from a MONO-Q column of a partially purified TK1 preparation corresponding approximately to fractions 201–204 of FIG. 2, subjected to a second run on a MONO-Q column as described in Example IV.

FIG. 3 depicts a chromatogram of absorbance vs. elution volume for the second sequential MONO-Q run. Fractions containing 1.0 ml of eluant were again collected. A major peak 300 eluted from the column at about 15% of Buffer B, and two minor peaks 302 and 304 eluted at about 18% and 20% Buffer B respectively. The peaks were assayed for TK1 activity and fraction 310 from the major peak 300 was determined to contain TK1 isozyme activity.

Protein from peak 300 (fractions 308, 310) was analyzed by SDS-PAGE and found to contain 3 proteins of molecular weights of about 100,000, 75,000, and 24,000, respectively. Upon assay for TK1 activity of protein from each of the bands, only the 100,000 dalton protein exhibited detectable TK1 activity.

Figure 4:
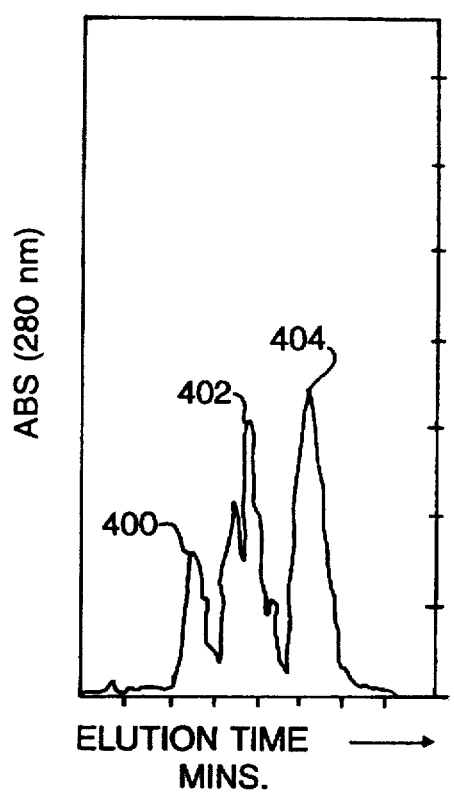
FIG. 4 is a chart depicting absorbance at 280 nm plotted versus elution time from a MONO-Q column of a further purified TK1 preparation corresponding approximately to fractions 308,310 of FIG. 3, and subjected to a third run on a MONO-Q column as described in Example IV.
Figure 5:
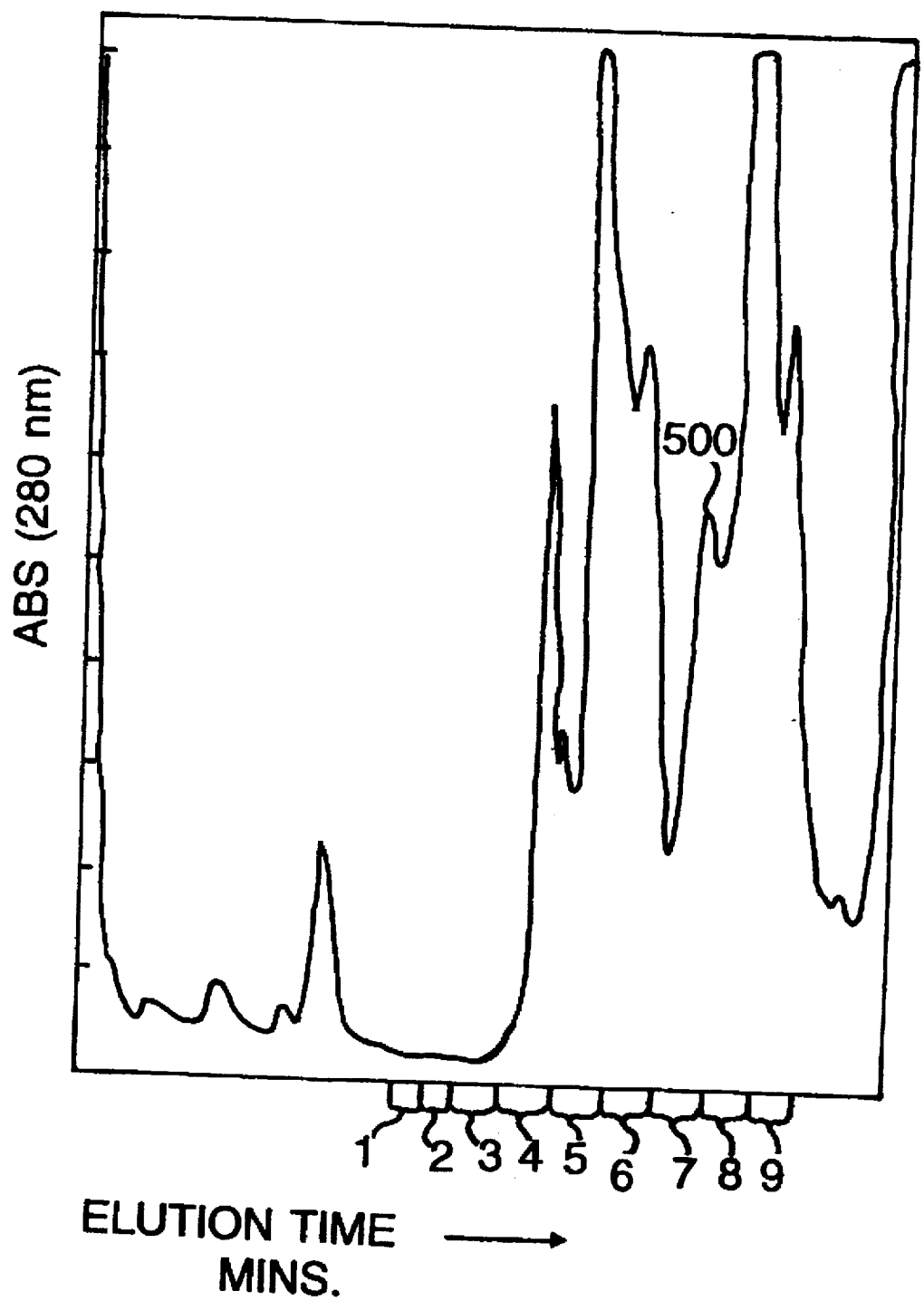
FIG. 5 is a chart depicting absorbance at 280 nm plotted versus elution time from a MONO-Q column of a crude extract of TK prepared from HeLa cells and run as described in Example IX.

A third sequential MONO-Q run was performed on protein precipitated and pooled from fractions 308, 310 containing the peak 300. The running conditions were further changed by slowing the flow rate and further decreasing the gradient. A gradient of 5% Buffer B to 30% Buffer B was run at 0.5 mls/min for 50 minutes. For this run, 0.5 ml fractions were collected. As shown in FIG. 4, there were three peaks 400, 402, 404 eluting near 15% of Buffer B. Protein from each of peaks 400, 402,404 was assayed for TK1 activity as before. The first peak 400 to elute contained TK1 activity, and when analyzed by non-denaturing PAGE was found to contain a single band at a molecular weight of about 100,000. This preparation is designated herein as "purified" TK1 isozyme. About 5 nanograms of protein with a specific activity of about 2,412,800 cpm/mg protein/min, were recovered in peak 400.

The protein from peak 400 from several column runs was pooled and analyzed by electrophoresis under reducing and non-reducing conditions. Only one band at 100,000 MW was observed on the non-reducing gel, while a faint band at 100,000 MW and a darker band at 24,000MW were observed on the reducing gel. From this result it appears that the active form of TK1 may be a multimer with subunits of lower molecular weights. The subunits also appear at present to be of identical molecular weights.

Presently, the procedure of Example 4 using the FPLC with MONO-Q column is the preferred method for isolating pure TK1. In Example 4, the starting material was the crude extract of Example 1. However, alternatively the DEAE-cellulose preparation of Example 2 can be used as the starting material. For producing semi-pure TK1 for antigen injection into mice, however, the method of Example 2 may be used, or the product obtained by the second run on the MONO-Q column as in Example 4 is also suitable.

EXAMPLE 5

Production of monoclonal antibodies binding to TK1

Hybridoma cell lines producing antibodies to TK1 were produced by methods generally known in the art, but with certain modifications.

TK1 was prepared as in Example 2. A dose of 100 µg of TK1 suspended in 50 µl of phosphate buffered saline (PBS) and 50 µl complete Freund's adjuvant was given intraperitoneally (I.P.) to each of a group of female BALB/c mice, 5–6 weeks old. Two weeks later, a second immunization was given that was identical to the first.

Two weeks following the second immunization with semi-pure TK1, an intrasplenic injection was given which contained 10 µg of pure active TK1 (prepared as in Example 4) suspended in 100 µl of PBS. The mice were anesthetized with sodium pentobarbital (65 mg/ml) which was diluted by adding 6.7 mls to 93.3 mls of PBS. Each mouse was given 10 µl/gram of body weight I.P. Surgical intervention was performed using a scalpel and forceps, and the spleen was gently teased out for administration of the antigen. Several areas of the spleen were injected to ensure uniform distribution of the antigen. The wound was closed with metal sutures and the mice were placed under a heating lamp for 1–2 hours.

Seventy-two hours following the intrasplenic injection, the mice were sacrificed using ether and the spleen was removed. Before the mice were killed, blood was removed and the serum tested to ensure that the mice were mounting an immune response to the TK1 protein. The B cells were isolated from the spleen for fusion with an immortal myeloma cell line.

The cell line used for the fusion partner was a self-fused Sp2/0 line designated FO which was purchased from ATCC.

It is a derivative of P3-X63-Ag8. This line is an immortal myeloma mouse cell line that is fast growing and a non-secretor (heavy or light chain immunoglobulins). The fusion of FO and activated spleen cells was performed generally as known in the art. One spleen containing about 1×10$^8$ cells was used per fusion. The most successful fusions resulted when the ratio of B-cells to FO cells was about 10:1. After the fusion was terminated, the fusion cell suspension was seeded into 96-well microtiter plates which had been seeded a day earlier with 3,000 to 6,000 mouse macrophages per well as feeder cells.

HAT selection medium was used to select only fusion products. Wells were marked for growth and gradually weaned out of HAT and into regular media. By this time the only surviving cells were hybridomas obtained by fusion of B-cells and FO cells. A total of about 500 colonies representing fusion products resulted from each fusion.

EXAMPLE 6

Preliminary screening of hybridoma colonies from fusion

Five hundred colonies from one fusion were subjected to preliminary screening by ELISA against partially purified TK1 prepared as in Example 2. Supernatants collected from the hybridoma cultures were initially screened with semi-pure TK1 prepared by running the crude extract of Raji cells on DEAE cellulose to partially purify the TK1. Thus, this preliminary screen is used as an initial detection of antibodies immunoreactive with TK1.

Multiwell plates were coated with 1.0 µg (micrograms) per well of selected TK1 protein preparations suspended in 50 µl PBS, and allowed to dry overnight. The plates were then treated for 30 minutes with 200 µl per well of PBS-TWEEN 20®-EDTA-1% milk fat to block non-specific binding. The plates were washed three times with 200 µl of PBS-TWEEN 20® EDTA (PBST2E). (TWEEN 20® is an anionic detergent commercially available from Bio-Rad Laboratories, Richmond, Calif., and useful to reduce non-specific antibody-antigen binding while not disrupting binding of primary antibodies to antigens or of antigens to nitrocellulose.)

The growth medium on the hybridoma cell cultures was not changed for three days prior to collection of the hybridoma culture supernatants in order to saturate the media with antibodies. For each hybridoma, 80 µl of supernatant per well was added to duplicate wells. The multiwell plates were then incubated at 37° C. for one and a half hours. The supernatant was decanted and the wells washed six times with PBST2E.

Next, goat anti-mouse IgG (heavy and light chain specific) conjugated with peroxidase (available from Bio-Rad) and diluted 1:3,000 in PBST2E was added. One-tenth ml was added to each well and the plates incubated as before. The wells were again washed in PBST2E and 200 µl of substrate, tetramethyl-benzidine, was added and incubated for 1 hour. The substrate reaction was stopped by adding 50 µl of 2M sulfuric acid to each well to cause a color shift from blue to yellow. The plates were scanned for O.D. measurement at 450 nm on a plate reader. O.D. readings that were at least twice the background O.D. were deemed positive. Of about 25,000 clones obtained from fifty fusions, 35 tested positive in the preliminary screening. The positive colonies were isotyped using a kit from Hyclone, Logan, Utah (cat. # EK-5051), and the positive colonies were determined to produce antibodies of IgG1, IgG2a, IgG3, and IgM classes.

EXAMPLE 7

Additional screening for TK1-specific hybridomas

The 35 clones which tested positive in the initial screenings were subjected to more rigorous screening. A plate was coated with five pairs of replicate wells as follows: wells A,B were coated with a crude extract of TK1 from Raji cells; wells C,D were coated with TK1 prepared from the DEAE-cellulose column; wells E,F were coated with purified TK1 from peak 400 prepared as in Example 4 by FPLC (see FIG. 4); wells G,H were coated with TK1 protein from fractions 308, 310 of the second FPLC run (see FIG. 3); and wells J,K were coated with an extract of E. coli cells which expressed a TK1 gene in a PET vector. For the purified samples, 1.0 µg per well of protein was used.

The ELISA was performed essentially as described for the preliminary screening. Of the 35 clones tested, one proved to bind only to active form TK1. The absorbance readings (ABS) were made at 405 nm for 120 wells on one plate on which ten clones were screened are shown in Table 1. The clones testing most highly positive by preliminary screening were purposely clustered on this plate. The background ABS from four wells was averaged and found to be about 0.058 (wells J11, J12 and K11, K12).

TABLE 1

Screening of Hybridoma Clones for Anti-TK1 Antibodies

| TK Prep | Clone Number | | | | | | | | | | | |
|---|---|---|---|---|---|---|---|---|---|---|---|---|
| | 1 | 2 | 3 | 4 | 5 | 6 | 7 | 8 | blank | blank | 11 | 12 |
| A | .196 | .204 | .137 | .227 | .165 | .055 | .090 | .067 | .075 | .057 | — | — |
| B | .403 | .181 | .117 | .172 | .153 | .049 | .091 | .068 | .086 | .050 | — | — |
| C | .061 | .109 | .050 | .156 | .119 | .041 | .048 | .048 | .045 | .039 | — | .000 |
| D | .078 | .117 | .063 | .090 | .158 | .046 | .049 | .046 | .046 | .046 | — | — |
| E | .114 | .150 | .085 | .116 | .157 | .043 | .046 | .114 | .083 | .056 | — | — |
| F | .160 | .142 | .083 | .127 | .218 | .050 | .114 | .076 | .081 | .045 | — | — |
| G | .093 | .128 | .081 | .135 | .164 | .057 | .076 | .071 | .086 | .048 | — | — |
| H | .107 | .141 | .097 | .153 | .222 | .056 | .071 | .059 | .065 | .051 | — | — |
| J | .240 | .291 | .188 | .195 | .225 | .063 | .116 | .068 | .077 | .126 | .054 | .071 |
| K | .243 | .197 | .195 | .182 | .215 | .077 | .124 | .073 | .074 | .069 | .058 | .082 |

Values given are the O.D. measured at 405 nanometers for samples assayed by ELISA with different TK1 preparations.
— refers to "not determined."

It will be apparent that positive binding (absorbance significantly greater than the background level) was observed in all the wells in columns 2 and 5; in all but rows C,D of column 1; in rows J,K of columns 3, 4 and 7; and in rows A,B of columns 4 and 7. That is, the clones in columns 1–5 and 7 all tested positive for binding to TK1. Of these, clones 2 and 5 tested positive for binding to all of the TK1 preparations tested, while clone 1 bound to all the TK1 preparations except the semi-purified DEAE-cellulose preparation. Clones 4 and 7 bound to the crude Raji cell TK1 extract and to the TK1 produced by genetic engineering in E. coli. Clone 3 bound only to the TK1 produced from E. coli. The remaining 25 clones tested negative for antibodies to TK1.

Further characterization was performed by Western blotting. The Western blots were prepared by procedures similar to those described in Current Protocols in Immunology, Vol. 1, publ. Wiley-Interscience, New York (1991). Antibodies were harvested from the supernatant of each hybridoma and hybridized to a nitrocellulose membrane blotted from a non-denaturing gel of TK proteins. A goat anti-mouse IgG was then used for detection of the bound antibodies.

In a blot obtained by electrophoresis of a sample of Raji extract, it was observed that the Clone 1 antibody bound only to the 100,000 dalton band known to have activity. Clone 5 antibody also bound only to this band, but less strongly. Clone 2 antibody bound to four bands of molecular weights about 24,000, 48,000, 72,000 and 100,000. These are believed to represent monomer, dimer, trimer and multimer forms of TK1. Thus, the Clone 2 antibody binds to all the commonly observed forms of TK1, or "total" TK1.

Another Western blot was prepared on a gel comprising the purified TK1 from the third run of the FPLC procedure (peak 400 in FIG. 4). This purified TK1 migrates as a homogeneous species at a molecular weight of 100,000, but has considerably less activity than was expected. Thus, this preparation is a multimer or tetramer form of TK1 but may not be in the active configuration. In this blot, the Clone 5 antibody bound strongly to the one band at 100,000, while the Clone 1 antibody bound less strongly to the band—the opposite of the result obtained in the blot of Raji cell extract.

From these results it can be seen Clone 1 and Clone 5 bind to different epitopes. The Clone 1 antibody binds specifically to the highly active tetrameric form of TK1 and is designated hereinafter as an "anti-AcTK1" antibody. Clone 5 antibody also binds to the multimer form but apparently to a less active multimer form.

Clones 1–5 are all IgM-type hybridomas. Clone 7 is an IgG-type hybridoma. Clones 1, 2 and 5 are on deposit with the American Type Culture Collection, Rockville, Md., as hybridoma strains HB 11432, HB 11433 and HB 11434, respectively.

EXAMPLE 8

Inhibition of TK1 activity by selected monoclonal antibodies

To test for inhibition of TK1 activity, the TK assay using ATP was performed using the crude extract of Raji cells as described above in Example 1. Replicate assay reactions were prepared. To designated reactions, a 20 μl aliquot of supernatant from one of the hybridoma cultures was added, containing between about 0.02 to 0.1 μg of antibody.

The incorporation of radioactivity was compared for control (no antibody) and test reactions to which hybridoma supernatant from selected hybridoma cultures had been added. The results obtained for pertinent hybridomas are summarized in Table 2.

TABLE 2

| TK1 Inhibition by Anti-TK1 Antibodies in the Raji Extract Assay | |
|---|---|
| Positive control | 56,103 cpm |
| Negative control* | 54,327 cpm |
| Clone #1 | 2,012 cpm |
| Clone #2 | 1,557 cpm |
| Clone #5 | 1,743 cpm |
| Clone #7 | 5,067 cpm |
| Clone #4 | 10,338 cpm |
| Clone #3 | 7,252 cpm |
| Clone #19 | 53,109 cpm |

*Supernatant from hybridoma cells producing antibodies not binding to TK enzymes.

In the reaction tubes to which were added supernatant samples from clones 1–5 and 7, the amount of radioactivity incorporated was no more than 20% of the amount of radioactivity in the controls. In contrast, supernatant from clone 19, one of the fusion products which tested negative by ELISA for TK1 binding, did not inhibit activity of TK1 in the Raji cell extract. It was also found that the ability to inhibit TK1 in this assay was positively correlated with the highest O.D. readings as determined by the ELISA method.

Antibodies from clones 3, 4, 6 and 7 were less efficient in inhibiting TK1 activity in the Raji extract assay. Therefore, they were not subjected to further screening.

Clones 1, 2 and 5 were again subjected to limiting dilution and colonies derived from this re-cloning procedure were tested once again. The re-cloning procedure was used to ensure that a hybridoma cell line is derived from a single fusion cell and thus produces antibodies which are uniform in isotype and specificity, e.g., monoclonal.

Clones 1, 2 and 5 were placed on deposit with the American Type Culture Collection on Aug. 11, 1993, as Nos. HB 11432, 11433, and 11434, respectively.

EXAMPLE 9

Isolation of TK2

Isolation of TK2 was performed by FPLC with a MONO-Q column. The starting material was a crude cell extract from HeLa cells prepared essentially as the Raji extract in Example 1. HeLa is an immortalized human cervical carcinoma cell line available from ATCC under the #CC1-2, which is believed to have high levels of TK2 and very low levels of TK1. When analyzed by non-denaturing PAGE, TK2 also appears to have a monomer form and one or more multimer forms.

As a preliminary step, a crude extract of HeLa cells was run on DEAE-cellulose. Using the CTP assay, the TK2 activity was found to be largely in peaks 18–20, which is quite separate from the region in which TK1 elutes.

Figure 6:
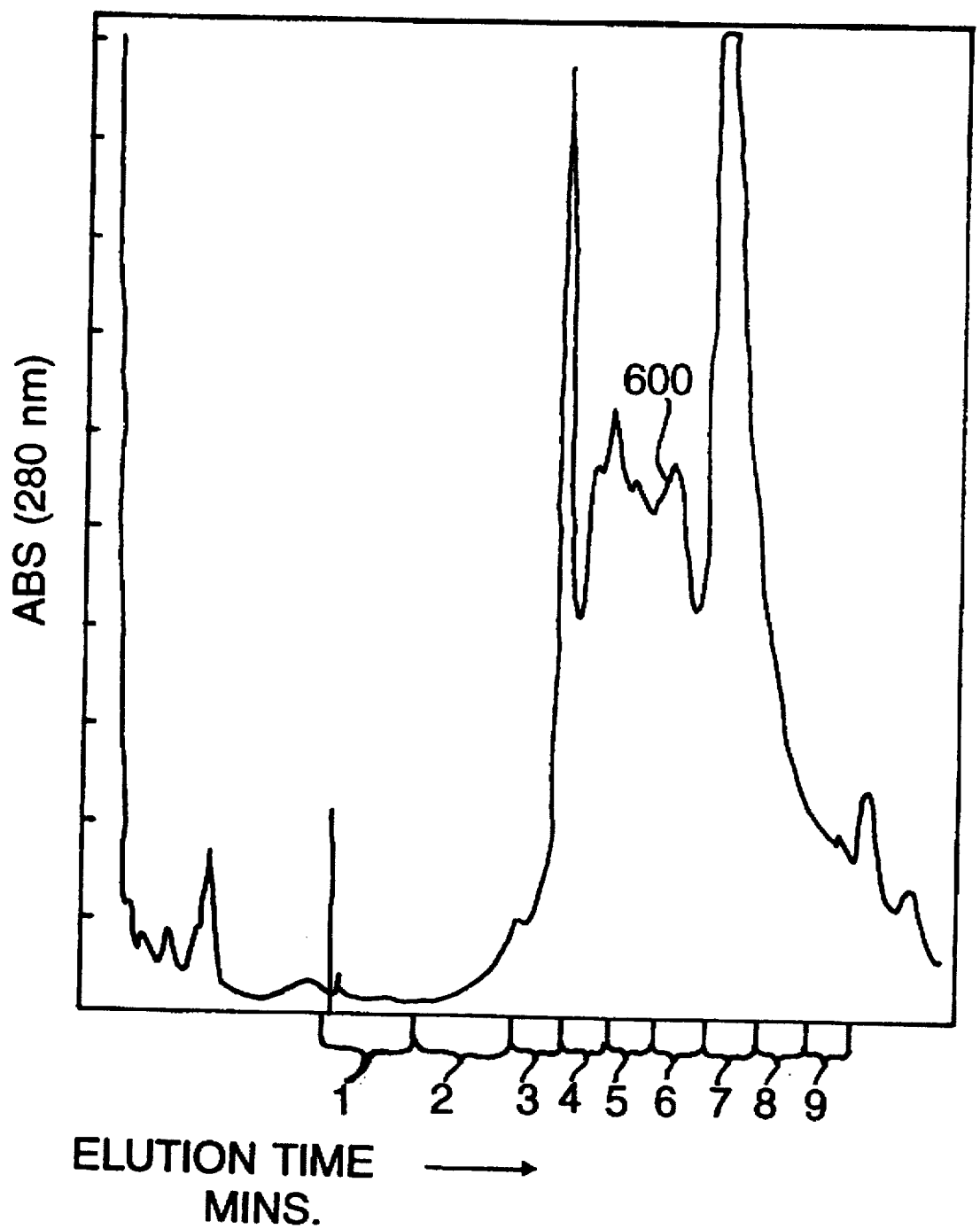
FIG. 6 is a chart depicting absorbance at 280 nm plotted versus elution time from a MONO-Q column of a partially purified TK2 preparation corresponding approximately to fractions 501–504 of FIG. 5, subjected to a second run on a MONO-Q column as described in Example IX.

Further purification was by FPLC on a MONO-Q column. FIG. shows the results of a first run on a MONO-Q column of pooled material from peaks 18–20. Buffer A was 0.05M Tris-HCl and Buffer B was 0.5M Tris-HCl. The column was run with a gradient of 5% to 45% Buffer B at a flow rate of 1 ml/min. The TK2 activity was assayed in the collected fractions and found to be mostly in fraction 7 (peak 500). Material from peak 500 from several column runs was pooled, concentrated and run a second time with the same buffer gradient and flow rate. FIG. 6 shows the results of the second run. The TK2 activity was found to be in fraction 6

(peak 600). The collected material of fraction 6 is a semi-pure preparation of active TK2 isozyme.

EXAMPLE 10

Monoclonal Antibody Specific to TK2

A preparation of TK2 comprising fraction 6 from the second run of the MONO-Q FPLC procedure in Example 9 was used as the antigen. The immunization procedure, harvest of spleen cells and fusion with FO cells was similar to that in Examples 5 and 6. Screening was performed by ELISA on wells coated with the semi-pure TK2 preparation of Example 4, and the results are given in Table 3. The results indicated that antibodies from Clones 2-2, 2-3, 2-4, 2-5, 2-7, 2-8, 2-9, 2-10, 2-12, 2-17 and 2-19 gave the most positive results for binding to the semi-pure TK2. In Table 3, the samples designated "2-1A," "2-5A," etc., represent separate replicate aliquots of antibody from Clones 2-1, 2-5, etc. Clones 2-7, 2-8, 2-9, 2-10 and 2-12 ultimately yielded hybridoma cell lines producing acceptable levels of anti-TK2 antibodies.

TABLE 3

Screening of Hybridoma Clones for Anti-TK2 Antibodies*

| Clone | 2-1 | 2-5 | 2-9 | 2-13 | 2-17 | 2-1A | 2-5A | 2-9A |
|---|---|---|---|---|---|---|---|---|
| O.D. 450 | 0.460 | 0.781 | 0.377 | 0.361 | 0.757 | 0.952 | 0.973 | 0.232 |
|  | 0.493 | 0.796 | 0.389 | 0.346 | 0.707 | 0.896 | 1.006 | 0.204 |
| Clone | 2-2 | 2-6 | 2-10 | 2-14 | 2-18 | 2-2A | 2-6A | 2-10A |
| O.D. 450 | 0.779 | 0.644 | 0.316 | 0.422 | 0.448 | 0.951 | 0.240 | 0.724 |
|  | 0.781 | 0.581 | 0.298 | 0.395 | 0.464 | 0.912 | 0.250 | 0.636 |
| Clone | 2-3 | 2-7 | 2-11 | 2-15 | 2-19 | 2-3A | 2-7A | 2-11A |
| O.D. 450 | 0.800 | 0.660 | 0.274 | 0.438 | 0.825 | 0.981 | 0.877 | 0.197 |
|  | 0.753 | 0.641 | 0.237 | 0.450 | 0.786 | 0.997 | 0.861 | 0.175 |
| Clone | 2-4 | 2-8 | 2-12 | 2-16 | 2-20 | 2-4A | 2-8A | — |
| O.D. 450 | 0.731 | 0.194 | 0.182 | 0.447 | 0.500 | 1.020 | 0.714 | 0.163 |
|  | 0.698 | 0.214 | 0.204 | 0.485 | 0.600 | 1.021 | 0.701 | 0.199 |
| Control | — | — | — | — | — | — | — | — |
| O.D. 450 | 0.079 | 0.084 | 0.090 | 0.083 | 0.078 | 0.080 | 0.076 | 0.082 |
|  | 0.074 | 0.073 | 0.071 | 0.082 | 0.076 | 0.076 | 0.076 | 0.078 |

*Two replicate wells per dilution were analyzed.

For use in tests with patient samples, the selected antibody-producing cell lines were passaged and supernatant was aseptically collected over a period of three months. Antibodies were purified by precipitating the supernatants with ammonium sulfate followed either by gel filtration chromatography or by DEAE-cellulose chromatography (diethylaminoethyl cellulose, obtained from Whatman International, Maidstone, Kent, UK under the tradename SEPHADEX). The antibodies were purified by standard methods and conjugated with either HRP-peroxidase or alkaline phosphatase (Bio-Rad). Such procedures are described in ANTIBODIES: A Laboratory Manual, by Harlowe and Lane, 1988.

For the determination of serum TK levels in human subjects, fresh samples of peripheral venous blood are collected from the subjects. Serum and mononuclear leukocytes are separated from each sample by conventional methods, and the separated samples are stored frozen until analysis. TK levels in tumor tissues can be determined by preparing an extract of TK from samples of fresh tumor tissue using a method similar to that for the crude extract of Raji cells of Example 1. Preferably, the protein content of the sample is determined so that the amount of TK can be correlated with the amount of total protein in the tumor. An immunoprecipitation assay using the desired anti-TK antibody can then be performed on the extract.

EXAMPLE 11

Histological detection of TK1

The conjugated antibody from Clone 1 was used to immunostain tumor cells histologically fixed to slides. Diaminobenzidine (DAB) was used as the enzyme substrate in this procedure.

EXAMPLE 12

Detection of active TK1 in serum samples from cancer patients using anti-At TK1 antibody.

It has been established that TK activity is elevated in the serum of patients with different kinds of cancer, for example as shown in Table 4. For the most part, sera of patients with cancer showed an elevated TK1 activity compared to control patients.

TABLE 4

Level of TK1 Activity in Sera*
From Controls and Patients with Different Cancers

| Patients | No. of Patients | TK Activity CPM ml$^{-1}$ Min$^{-1}$ | % TK2 | % TK1 |
|---|---|---|---|---|
| Controls | 34 | 274.04 | 72.70 | 27.30 |
| All Cancer | 76 | 425.11 | 53.48 | 46.52 |
| Breast | 20 | 469.23 | 59.75 | 40.25 |
| Body Uterus | 3 | 440.30 | 56.67 | 43.33 |
| Thyroid | 1 | 363.07 | 26.00 | 74.00 |
| Hypernephroma | 1 | 355.22 | 62.00 | 38.00 |
| Simple Skin | 4 | 407.31 | 40.75 | 59.25 |
| Lung | 2 | 322.64 | 62.00 | 38.00 |
| Non-Hodgkin' Lymphoma | 4 | 420.84 | 37.98 | 62.02 |
| Bone | 1 | 990.34 | 58.00 | 42.00 |
| Bladder | 6 | 440.39 | 71.33 | 28.67 |
| Squamous Cell | 6 | 307.26 | 48.33 | 51.67 |
| Rectal | 4 | 349.69 | 72.00 | 28.00 |
| Prostate Carcinoma | 5 | 461.66 | 47.00 | 53.00 |
| Cervix Carcinoma | 6 | 524.00 | 47.00 | 53.00 |
| Hodgkin's Lymphoma | 1 | 324.76 | 37.00 | 63.00 |
| Testicle | 2 | 171.20 | 69.50 | 30.50 |
| Brain | 6 | 339.33 | 42.67 | 57.33 |
| Basal Cell | 2 | 706.04 | 27.50 | 72.50 |
| Stomach | 1 | 541.93 | 27.00 | 73.00 |
| Benign | 1 | 407.50 | 76.00 | 24.00 |

*K. L. O'Neill (1986) Doctoral Thesis, University of Ulster, Coleraine, Northern Ireland A similar correlation between serum TK1 values and the presence of cancer was obtained using anti-TK1 monoclonal antibodies for measurement of TK1. Serum samples were obtained from cancer patients. Each sample was assayed for TK activity by a method like that of Example 1. The same samples were then quantitated blindly on an ELISA test with Clone 1 antibody using different serum dilution levels. A dilution of 1:16,000 was found to give the best results. The results of the two assays are presented in Table 5. The data were confirmed by Western blot analysis.

TABLE 5

Comparison of TK1 Activity Measured by $^3$H-thymidine Incorporation and Anti-AcTK1 Antibody Binding

| Serum # | TK1 assay | Rank* | O.D. 450 nm |
|---|---|---|---|
| 1 | 2498 | 5 | .443 |
| 2 | 2376 | 5 | .430 |
| 3 | 8251 | 2 | .865 |
| 4 | 6254 | 3 | .728 |
| 5 | 2214 | 5 | .420 |
| 6 | 11477 | 1 | 1.542 |
| 7 | 2509 | 5 | .450 |
| 8 | 4785 | 4 | .592 |
| 0[1] | — | 8 | .250 |

The O.D. 450 readings represent the amount of bound Clone 1 antibody measured by ELISA. The TK activity values are the cpm of $^3$H incorporated per minute.
*determined from the ELISA data
[1]Healthy (non-cancer) control In Table 5, the sera are ranked from highest to lowest amount of anti-TK1 bound, by the O.D. reading in the ELISA assay. It can be seen from the TK1 activity measurements that the correlation is excellent between antibody binding data and the standard TK1 activity assay. The data demonstrate that the anti-AcTK1 antibody can be used to evaluate the serum level of TK1 activity in human subjects. Further, serum from a healthy (non-cancer-bearing) individual bound much less anti-AcTK1 antibody as compared to the lowest-ranked serum of a cancer patient. Thus, the anti-AcTK1 antibody is useful to distinguish between serum of cancer-bearing individuals and serum from healthy non-cancerous individuals.

EXAMPLE 13

Prediction of recurrence of tumor in a patient with a primary tumor

It has been further found that the levels of TK activity, and particularly of TK1 activity, can be used as a reliable predictor of the likelihood of tumor recurrence in breast cancer patients. Table 6 summarizes the results of a study of TK activity in samples from untreated primary tumors that were surgically removed from 86 patients, 13 of which later experienced a recurrence of disease.

TABLE 6

Tumor TK levels and recurrence

| Patients | Number | Total Tumor TK* | Statistical Significance | % TK2 | Statistical Significance |
|---|---|---|---|---|---|
| No recurrence | 73 | 144961.9 | p < 0.001 | 74.5 | p < 0.001 |
| Recurrence | 13 | 351693.5 | | 41.7 | |

*cpm/min of reaction time per mg protein

In this study recurrence was compared not only with TK levels but also with the art-recommended diagnostic assay, the estrogen receptor status. As shown in Table 7, the TK level in the tumor sample accurately predicted which patients in the estrogen receptor positive group later showed recurrence and which in the estrogen receptor negative group did not show recurrence.

TABLE 7

Correlation of Estrogen Receptor and TK Levels with Recurrence

| Estrogen Receptor Level in 86 Patients | | Recurrence of Tumor | | TK Activity | % TK2 | TK1 Activity |
|---|---|---|---|---|---|---|
| High | Low | Yes | No | | | |
| 57 | | | 4 | 289,717 | 41 | 170,933 |
| | | | 53 | 161,674 | 76 | 38,802 |
| | 29 | 9 | | 379,238 | 42 | 219,958 |
| | | | 20 | 100,675 | 71 | 29,196 |

Of 57 estrogen receptor positive patients (patients whose tumors had high numbers of estrogen receptors), four had recurrence of disease. The average TK activity level measured in the tumors from those four patients was 289,717 cpm/min, as compared with 161,674 cpm/min for tumors from patients who had no recurrence. Also, the percentage of the activity attributable to TK2 was about 76% in the no-recurrence group vs. 41% in the four who had recurrence.

Conversely, of 29 estrogen receptor negative patients (those whose tumors had few or no estrogen receptors), the 20 who did not have recurrence had an average TK activity level of 100675 cpm/min with about 71% being TK2 activity, as compared to 379238 cpm/min with about 42% being TK2 activity for the group that did have recurrence. Thus, the level of TK activity and the relative proportions of TK2 to TK1 activity were both better predictors of recurrence than estrogen receptor status.

A more exacting correlation was obtained between recurrence of tumor and the elevated level of TK1 activity. As shown in Table 7, the level of TK1 activity in patients showing recurrence of tumor was between about five- and about eight-fold higher than in patients with no further recurrence of tumor. According to the instant invention, determination of TK1 activity using anti-TK1 monoclonal antibody correlates exactly with determinations using TK1 enzyme activity assays. Thus, determination of levels of TK1 activity in patient samples can be carried out using anti-TK1 monoclonal antibodies of the invention to diagnose the presence of cancer in a patient and/or to predict the likelihood of cancer recurrence.

Measurement of TK1 activity in body fluids of patients having primary tumors is also indicative of the likelihood of tumor recurrence. For example, with respect to leukemia patients, it has been found that the level of TK1 activity in serum can be used to detect relapse, often before any other symptom is evident.

The anti-TK1 antibody, and particularly the anti-AcTK1 antibody, is useful to screen serum and tissue from cancer patients both for prognostic purposes and for use in diagnosis and treatment of tumor patients. Anti-TK1 antibodies may also be useful for serum screening in certain other kinds of blood disorders, such as pernicious anemia, where fluctuation in TK activity has been linked to disease status. The antibodies may further be useful for testing of patients with certain viral diseases including morbilli, rubella and herpes, where it has been found that the levels of thymidine kinase are elevated during the acute phase of the disease.

Because the anti-AcTK1 antibody detects only the active 100 kD form of TK1, it can be used in place of the routine radioactive thymidine incorporation assay to evaluate specifically TK1 activity. The use of the antibodies of the invention for evaluating TK1 activity in tumors and serum of cancer patients makes it practical for screening on a wide scale, whereas screening using enzyme activity assay is generally more difficult and time-consuming to perform.

Also, the anti-TK1 antibody, and particularly the anti-AcTK1 antibody, is useful for targeted tumor therapy. For example, the anti-AcTK1 antibody may be used to inhibit the elevated level and to restore a normal level of TK1 enzyme activity in the tumor cells. Further, an anti-tumor agent may be coupled to the anti-TK1 antibody, which binds specifically to tumor cells expressing large amounts of TK1. In this manner the anti-tumor agent is targeted to specific tumor cells and thus the killing of these tumor cells is preferentially enhanced relative to the killing of normal cells.

The invention is further embodied as methods and kits for performing the methods. A method of determining the serum level of a thymidine kinase enzyme comprises the following steps: obtaining a serum sample from a patient, providing a monoclonal antibody which specifically binds to thymidine kinase enzyme, contacting the monoclonal antibody with the sample, and determining the amount of monoclonal antibody bound to thymidine kinase protein in the sample.

An alternate embodiment is a method for evaluating the level of thymidine kinase in a solid tumor sample. This method is essentially the same as that for evaluating serum thymidine kinase levels, except that the step of providing a serum sample is replaced by a step of providing a tumor sample. The tumor sample may be a fresh or frozen tissue sample or a histological slide preparation.

A kit for performing the above methods may comprise one or more monoclonal antibodies, for example, anti-TK1 antibody with or without anti-TK2 antibody. In one embodiment, the monoclonal antibody is conjugated to an enzyme useful in an ELISA assay or to another detectable marker such as a fluorescent dye, radioactive isotope, or the like. Alternatively, the kit may further include an anti-mouse antibody which is enzyme-conjugated for detection by ELISA or otherwise labelled.

A method of predicting the likelihood of recurrence of a solid tumor in a patient at initial diagnosis comprises the steps of establishing a normal range for tissue TK activity, obtaining a sample of a primary tumor from a patient, determining the amount of TK enzyme in the patient sample to produce a patient TK value, and comparing the patient TK value to a normal value; and if it exceeds the normal range by a significant amount, predicting that the tumor is likely to recur, and if it does not significantly exceed the normal range, predicting that recurrence is unlikely. The step of establishing a normal range may be performed in several ways. In one embodiment, one or more samples of the patient's own normal tissue may be used for comparison. In another embodiment, a normal range may be established from a study of normal tissues in healthy (no disease) individuals, or from patients known to be in remission.

In a highly preferred embodiment, the TK measurement is specifically TK1 activity or a comparison of TK1 and TK2 activity levels is provided. In a further preferred embodiment, the level of active TK1 is measured using an anti-AcTK1 antibody. In bladder cancer, a preferred alternate embodiment employs an anti-TK2 antibody.

A method of determining whether disease has recurred in a patient being treated for a cancer or blood disorder, including breast cancer, leukemia and lymphoid cancer, comprises the steps of taking a series of samples of the serum of a cancer patient at regular intervals, measuring the amount of TK in the samples, comparing the amount of TK among the samples and, when the amount of TK in later samples exceeds the amount of earlier samples by a significant degree, determining that the disease is recurring. In preferred embodiments, the measurements are of TK1 activity in the sample as determined using an anti-AcTK1 monoclonal antibody.

What is claimed is:

1. A monoclonal antibody to a purified, approximately 100 kD, tetrameric form of a mammalian thymidine kinase 1 (TK1).

2. The monoclonal antibody according to claim 1 wherein said monoclonal antibody inhibits TK1 enzymatic activity.

3. The monoclonal antibody according to claim 1 wherein said monoclonal antibody inhibits TK1 enzymatic activity in a mammalian biological sample.

4. The monoclonal antibody according to claim 3 wherein said mammalian biological sample is a body fluid or a body tissue.

5. The monoclonal antibody according to claim 4 wherein said body fluid is selected from the group consisting of blood, serum, urine, and spinal fluid.

6. The monoclonal antibody according to claim 4 wherein said body tissue is a normal tissue or a tumorigenic tissue.

7. The monoclonal antibody according to claim 3 wherein said mammalian biological sample is from a human.

8. The monoclonal antibody according to claim 1 wherein said monoclonal antibody is an IgG or an IgM antibody.

9. The monoclonal antibody according to claim 1 wherein said monoclonal antibody is produced by a hybridoma selected from the group consisting of American Type Culture Collection hybridomas HB 11432, HB 11433 and HB 11434.

10. A hybridoma producing the monoclonal antibody of claim 1.

11. A hybridoma of claim 10 selected from the group consisting of American Type Culture Collection hybridomas HB 11432, HB 11433 and HB 11434.

12. A method of diagnosis of cancer in a patient having an elevated level of thymidine kinase 1 (TK1) activity in a biological sample from said patient, said elevated level being associated with the presence of said cancer, comprising the steps of:
   (a) establishing a normal TK1 value by determining with a monoclonal antibody to a purified, approximately 100 kD), tetrameric form of a mammalian TK1 the level of TK1 activity in a biological sample of a patient without cancer;
   (b) establishing said patient's TK1 value by determining with said monoclonal antibody the level of TK1 activity in said biological sample from said cancer patient; and
   (c) comparing said patient's TK1 value with said normal TK1 value to determine if said patient TK1 value is a normal level or an elevated level of TK1 activity, said elevated level being diagnostic of said cancer.

13. The method of diagnosis of cancer of claim 12 wherein said patient is a human.

14. The method of diagnosis of cancer of claim 12 wherein said cancer is selected from the group consisting of leukemia, lymphoma, and a solid tumor from breast, prostate, brain, thyroid, stomach or rectum.

15. The method of diagnosis of cancer of claim 12 where said cancer is breast cancer.

16. The method of diagnosis of cancer of claim 13 wherein said biological sample is selected from the group consisting of blood, serum, urine, spinal fluid, normal tissue and tumor tissue.

17. The method of diagnosis of cancer of claim 13 wherein said biological sample is serum.

18. A method of predicting the likelihood of recurrence of a tumor in a patient having a primary tumor, said primary tumor being associated with an elevated level of thymidine kinase 1 (TK1) activity, comprising the steps of:

(a) determining immunologically said patient's TK1 value with a monoclonal antibody to purified, approximately 100 kD, tetrameric form of a mammalian TK1;

(b) determining immunologically said patient's TK2 value with a monoclonal antibody to a purified mammalian thymidine kinase 2 (TK2);

(c) determining the level of TK1 activity as a percentage of the total (TK1+TK2) activity and determining the level of TK2 activity as a percentage of the total (TK1+TK2) activity; and (d) predicting a recurrence of said tumor in said patient, if said percentage of TK1 activity is equal to or greater than 40% and predicting a nonrecurrence of said tumor in said patient, if said percentage of TK1 is less than 40%.

19. A method of predicting the likelihood of recurrence of a tumor in a patient having a primary tumor, said primary tumor being associated with an elevated level of thymidine kinase 1 (TK1) activity, comprising the steps of:

(1) establishing for said tumor a level of elevated TK1 activity that is predictive of recurrence of said tumor and a level of baseline TK1 activity that is predictive of non-recurrence of said tumor in a method comprising the steps of:

(a) obtaining samples of untreated primary tumors that were surgically removed from cancer patients, some of whom had recurrence of said tumor and the remainder of whom did not exhibit recurrence of said tumor, and separating said samples into two groups, a first group of samples from cancer patients having recurrence of said tumor and a second group of samples from cancer patients not exhibiting recurrence of said tumor;

determining the level of TK1 in said samples of step (a) with a monoclonal antibody to a purified, approximately 100 kD, tetrameric form of a mammalian TK1;

(c) computing an average value of elevated TK1 levels for said first group and an average value of baseline TK1 ovals for said second group such that the average value of elevated TK1 levels for the first group is at least about two-fold higher than the average value of baseline TK1 levels for the second group; and (d) correlating said first group of elevated TK1 levels of step (c) with tumors from patients having recurrence of said tumor and correlating said second group of baseline TK1 levels of step (c) with tumors from patients not exhibiting recurrence of said tumor;

(2) using said monoclonal antibody to determine the level of TK1 in a biological sample of said patient having a primary tumor; and (3) predicting a recurrence of said tumor in said patient if the level of TK1 determined in step (2) is an elevated TK1 level as defined in step 1(c), and predicting a non-recurrence of said tumor in said patient if the level of TK1 determined in step (2) is a baseline TK1 level as defined in step 1(c).

20. The method of claim 19 wherein said biological sample is selected from the group consisting of blood, serum, urine, spinal fluid, normal tissue and tumor tissue.

21. The method of claim 19 wherein said average value for the first group of elevated TK1 levels is between about three- and about fifteen-fold higher than the average value of the second group of baseline TK1 levels in step 1(c).

22. A kit useful for the determination of the level of thymidine kinase 1 (TK1) in a mammalian biological sample; for the diagnosis of cancer in a patient having an elevated level of TK1 as compared with a normal level of TK1; for predicting the likelihood of recurrence of a tumor in a patient; and for predicting the likelihood of recurrence of a tumor in a patient having a level of TK1 about three- to about fifteen-fold higher than said normal level; said kit comprising:

a monoclonal antibody to a purified, approximately 100 kD, tetrameric form of a mammalian TK1, and a reagent useful for detecting the extent of interaction between said monoclonal antibody and said TK1 in said mammalian biological sample.

23. A kit useful for the determination of the level of thymidine kinase 1 (TK1) and the level of thymidine kinase 2 (TK2) in a mammalian biological sample; and for predicting the likelihood of recurrence of a tumor in a patient with a tumor, if the level of said TK1 in said tumor is equal to or greater than 40% of the total TK (TK1+TK2); said kit comprising:

a monoclonal antibody to a purified, approximately 100 kD, tetrameric form of a mammalian TK1;

a first reagent useful for detecting the extent of interaction between said monoclonal antibody to a purified TK1 and said TK1 in said mammalian biological sample;

a monoclonal antibody to a purified TK2; and a second reagent useful for detecting the extent of interaction between said monoclonal antibody to a purified TK2 and said TK2 in said mammalian biological sample.

24. The method of claim 12 wherein said biological sample is a histological preparation of a fresh or frozen tissue sample.

25. The method of claim 18 wherein said biological sample is a histological preparation of a fresh or frozen tissue sample.

26. The method of claim 19 wherein said biological sample is a histological preparation of a fresh or frozen tissue sample.

* * * * *